(12) United States Patent
Danby

(10) Patent No.: US 6,398,760 B1
(45) Date of Patent: Jun. 4, 2002

(54) VOLUMETRIC INFUSION PUMP WITH SERVO VALVE CONTROL

(75) Inventor: Hal C. Danby, Suffolk (GB)

(73) Assignee: Baxter International, Inc., Deerfield, IL (US)

( * ) Notice: Subject to any disclaimer, the term of this patent is extended or adjusted under 35 U.S.C. 154(b) by 0 days.

(21) Appl. No.: 09/410,676

(22) Filed: Oct. 1, 1999

(51) Int. Cl.⁷ .............................................. A61M 37/00

(52) U.S. Cl. ...................................... 604/132; 604/141

(58) Field of Search ................................ 604/131, 132, 604/133, 134, 135, 140, 141, 142, 143, 144, 67; 417/474–479

(56) References Cited

U.S. PATENT DOCUMENTS

| | | | |
|---|---|---|---|
| 3,640,277 A | | 2/1972 | Adelberg |
| 4,033,479 A | * | 7/1977 | Fletcher et al. ............... 222/61 |
| 4,769,008 A | | 9/1988 | Hessel |
| 4,955,860 A | | 9/1990 | Ruano |
| 5,163,909 A | | 11/1992 | Stewart |
| 5,302,093 A | * | 4/1994 | Owens et al. ............... 417/474 |
| 5,348,539 A | | 9/1994 | Herskowitz |
| 5,554,123 A | | 9/1996 | Herskowitz |
| RE35,501 E | * | 5/1997 | Ross et al. ................... 604/141 |
| 5,628,619 A | | 5/1997 | Wilson |
| 5,681,284 A | * | 10/1997 | Herskowitz ................. 604/141 |
| 5,749,854 A | | 5/1998 | Shen |
| 5,788,674 A | | 8/1998 | McWilliams |
| 5,853,386 A | * | 12/1998 | Davis et al. ................... 604/65 |

FOREIGN PATENT DOCUMENTS

EP 0 481 601 A2 4/1992

* cited by examiner

Primary Examiner—Glenn K. Dawson
Assistant Examiner—Jennifer Maynard
(74) Attorney, Agent, or Firm—Swanson & Bratschun LLC

(57) ABSTRACT

An infusion pump (10) includes a reservoir (18) containing a therapeutic liquid to be infused. The reservoir (18) includes an outlet (36) for the liquid. A volumetric air pump (24) is operatively associated with the reservoir (18) to pressurize the reservoir and thus drive liquid out the outlet (36). A valve (12) is operatively associated with the outlet (36) and prevents the flow of liquid through the outlet until a select threshold pressure is obtained in the outlet. The valve thereafter maintains an opening in the outlet that keeps the pressure in the reservoir (18) at substantially the select threshold pressure, whereby the volumetric flow rate of liquid through the outlet (36) is proportional to the volumetric flow rate of air from the volumetric air pump (24). The valve (12) varies the opening in the outlet to maintain the select pressure. The outlet preferably consists of a flexible conduit (36) having a select undeformed inner cross-sectional area and the valve (12) variably restricts the flow of liquid through the outlet by pinching a segment of the conduit to vary the inner cross-sectional area of the segment of the conduit. A method of infusing therapeutic liquid to a patient includes providing a reservoir (18) containing a therapeutic liquid, providing a volumetric air pump (24) to pressurize the reservoir to flow liquid out the liquid reservoir through an outlet (36) and maintaining a select pressure in the reservoir so that liquid through the liquid outlet is proportional to the volumetric flow rate of the volumetric air pump.

17 Claims, 1 Drawing Sheet

VOLUMETRIC INFUSION PUMP WITH SERVO VALVE CONTROL

RELATED APPLICATIONS

This application claims priority from United Kingdom Patent Application Serial No. 9916111.9, filed Jul. 10, 1999, entitled "Infusion Pump".

TECHNICAL FIELD

The present invention is directed toward volumetric infusion pumps, and more particularly toward a self-regulating servo valve for use with a volumetric infusion pump.

BACKGROUND ART

It is a common practice in the medical field for a therapeutic liquid to be delivered to a patient by subjecting the liquid to a known pressure and passing the liquid through a restricting device of known internal cross section to produce a reasonably constant flow rate. One manner of implementing this practice is providing and filling an elastomeric balloon with the therapeutic liquid under pressure to stretch the elastomeric balloon which, in turn, pressurizes the liquid. The liquid is then discharged through a restricting device. In practice, it has been found to be difficult to regulate the pressure on the liquid accurately over the full volume of the balloon because of the changing pressure applied to the therapeutic liquid as the elastomeric balloon changes shape during the course of an infusion. A representative apparatus for practicing this method of infusion is disclosed in Hessel, U.S. Pat. No. 4,769,008.

Another similar apparatus for infusing therapeutic liquids to a patient includes a collapsible bag containing the therapeutic liquid juxtaposed with an inflatable bladder, with the bladder and the collapsible bag being contained within a rigid housing. The bladder is inflated, for example with compressed air, to apply pressure to the collapsible bag and thus expel therapeutic liquid from it. The therapeutic liquid is expelled through an outlet tube having a fixed cross-sectional area or which includes a flow restrictor of a fixed cross-sectional area. Fluid is provided to the bladder at a controlled rate with the intent that fluid is thus forced through the outlet tube at an approximate flow rate. Representative patents disclosing this basic structure include Ross, U.S. Pat. No. Re 35,501 and McWilliams, U.S. Pat. No. 5,788,674. In practice, however, it has been found very difficult to provide a suitably constant low flow rate necessary for some clinical applications.

Shen, U.S. Pat. No. 5,749,854, attempts to overcome the deficiencies of the prior art by teaching a valve for controlling the flow of air into a bladder driving such an infusion pump. However, Shen requires a complicated and expensive valving mechanism and may still not provide a suitably constant low flow rate.

The present invention is directed toward overcoming one or more of the problems discussed above.

SUMMARY OF THE INVENTION

A first aspect of the present invention is an infusion pump including a reservoir containing a therapeutic liquid to be infused. The reservoir includes an outlet for the liquid. A volumetric air pump is operatively associated with the reservoir to pressurize the reservoir. A valve is operatively associated with the liquid outlet and prevents liquid flow through the liquid outlet until a select pressure is obtained in the outlet. The valve thereafter maintains an opening in the outlet that keeps the pressure in the reservoir at substantially the select pressure, whereby the volumetric flow rate of liquid through the outlet is proportional to the volumetric flow rate of air from the volumetric air pump. Preferably, the valve varies the opening in the outlet so as to maintain the select pressure. The outlet may consist of a flexible conduit having a select undeformed inner cross-sectional area and the valve varies the opening in the outlet by pinching a segment of the conduit to vary the inner cross-sectional area of the segment of the conduit. Preferably, the reservoir comprises a collapsible wall and the infusion pump further comprises an inflatable bladder juxtaposed with the collapsible wall of the reservoir. The volumetric air pump is in fluid communication with the bladder. The volumetric air pump provides gas to the bladder at a first rate until the select pressure is applied to the reservoir and thereafter provides gas to the bladder at a second substantially uniform rate less than the first rate.

A second aspect of the present invention is an infusion pump including a collapsible bag defining a therapeutic liquid reservoir, the collapsible bag having a resilient tubing defining a reservoir outlet extending therefrom. An inflatable bladder is juxtaposed with the collapsible bag. A rigid housing defines a chamber receiving the collapsible bag and the inflatable bladder and includes a port receiving the resilient tubing. A volumetric air pump is in fluid communication with the bladder to inflate the bladder and thereby apply pressure to the collapsible bag. A valve is operatively associated with the resilient tubing to variably restrict the flow of liquid through the resilient tubing as a function of the pressure applied to the collapsible bag to maintain the substantially constant select pressure in the collapsible bag. The valve preferably prevents the flow of liquid through the resilient tubing until application of the select pressure to the collapsible bag. The valve may consist of a blade and anvil receiving the resilient tubing therebetween. The blade is biased toward the anvil to restrict the flow of liquid through the resilient tubing and the blade is operatively associated with the collapsible bag to bias the blade away from the anvil as pressure within the collapsible bag increases. The volumetric air pump preferably provides gas to the bladder at a first rate until the select pressure sufficient to overcome the biasing force on the blade so as to initially move the arm and the blade away from the anvil is applied to the reservoir and thereafter provides gas to the bladder at a second substantially uniform rate less than the first rate. A detector may be operatively associated with the arm and the volumetric air pump with the detector detecting the initial movement of the arm and sending a first signal to the volumetric air pump. The sensor may further detect if the blade moves more than a select distance from the anvil, at which point a second signal is sent to the volumetric air pump.

A third aspect of the present invention is a method of infusing therapeutic liquid to a patient. The method includes providing a reservoir containing a therapeutic liquid and having a liquid outlet, providing a volumetric air pump in operative association with the reservoir to pressurize the reservoir and maintaining the select pressure in the reservoir so that liquid through the liquid outlet is proportional to the volumetric flow rate of the volumetric air pump. The liquid outlet may comprise a resilient tube and the method may further comprise applying a pinching force to a segment of the resilient tube and decreasing the pinching force as the pressure in the reservoir increases to increase an effective inner cross-sectional area of the segment of the resilient tube. The method may further comprise pressurizing the reservoir by providing a bladder juxtaposed with the reservoir in fluid communication with the volumetric air pump and preventing flow of liquid through the liquid outlet if the pressure in the reservoir is less than the select pressure. The method may further include inflating the bladder at a first rate until the select pressure is reached in the reservoir and thereafter inflating the bladder at a second substantially constant rate less than the first rate.

The infusion pump with servo valve control and method of infusing therapeutic liquid of the present invention provides a highly reliable manner to maintain constant flow rates from the infusion pump over a wide range of flow rates. By directly linking the effective inner cross-sectional area of the outlet to a select pressure applied to the collapsible reservoir, a select pressure at the outlet can be accurately maintained, thereby insuring a substantially constant flow rate by keeping the liquid volumetric flow rate proportional to the volumetric rate of air provided by the volumetric air pump. If the pressure in a line to a patient increases, for example, due to lowering of the pump relative to the point of infusion, pressure will build within the bag which will thereby cause the valve to open further, allowing for a gradually increasing flow rate until the pressure in the bag returns to the select pressure. In this manner, the pump is self regulating. If the valve opens beyond a select amount, indicating a downstream occlusion, the volumetric air pump stops operating, preventing an excessive pressure build up.

DETAILED DESCRIPTION OF THE PREFERRED EMBODIMENT

Figure 1:
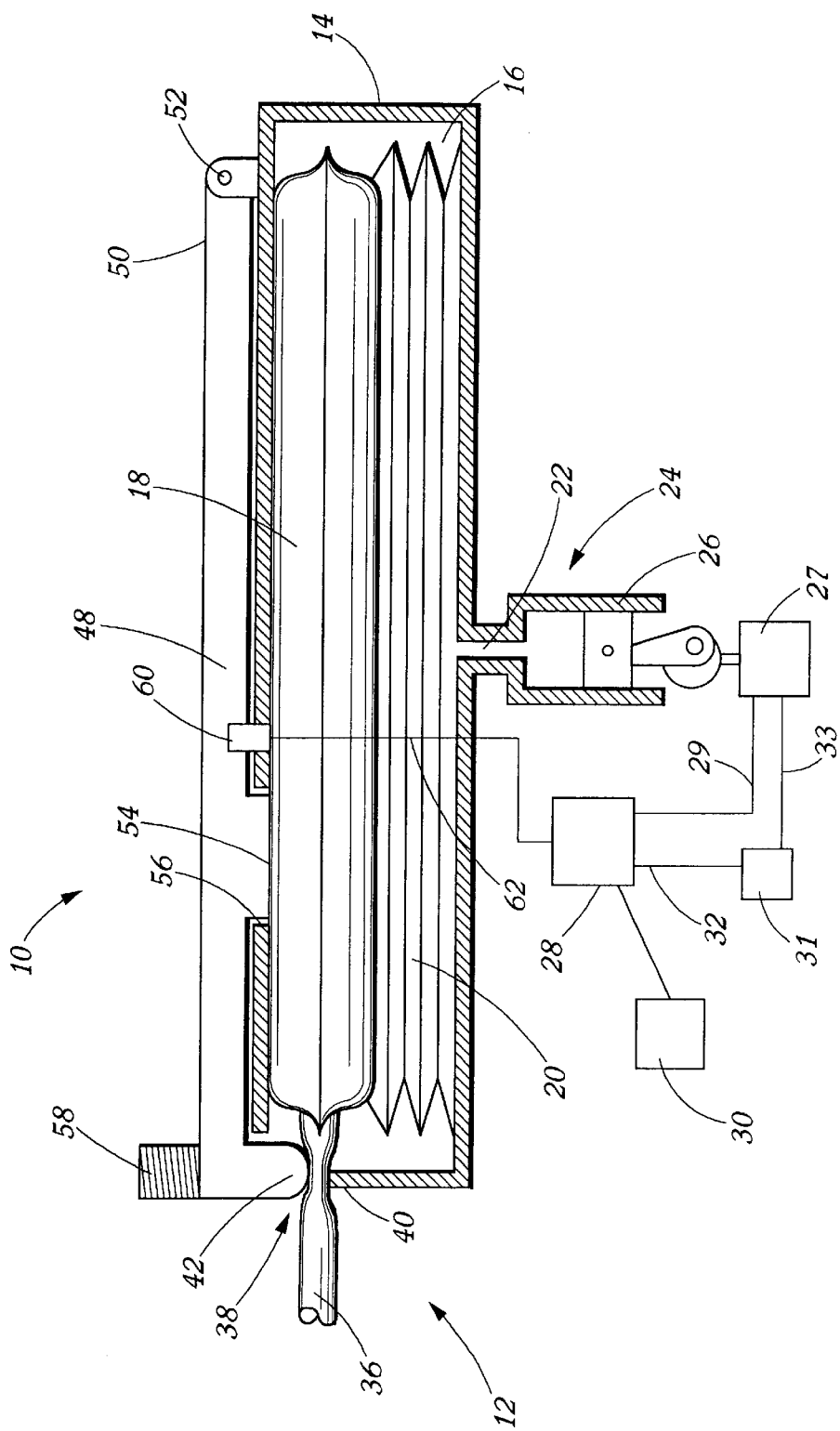
FIG. 1 is a schematic cross-sectional, elevational representation of the volumetric infusion with servo valve control of the present invention.

A volumetric infusion pump 10 including a servo valve 12 of the present invention is illustrated schematically in FIG. 1. The volumetric infusion pump 10 consists of a housing 14 defining a chamber 16 of a fixed volume. Within the chamber 16 is a collapsible bag 18 defining a reservoir for a therapeutic liquid. Also within the chamber 16 juxtaposed with the collapsible bag 18 is an inflatable bladder 20 in fluid communication by conduit 22 with a volumetric gas source 24. In the preferred embodiment, the volumetric gas source 24 consists of a volumetric air pump 26 driven by an encoded electric motor 27. The encoded electric motor 27 is coupled to a control circuit or microprocessor 28 by a connector 29. The microprocessor 28 may be preprogrammed or alternatively reprogramable through input station 30. The microprocessor 28 and electric motor 27 are preferably powered from a single power supply 31 which distributes power via lines 32 and 33. The power supply 31 may be an internal battery which can be replaceable, rechargeable or disposable along with the entire infusion pump 10. Alternatively, the power supply can be external to the pump 10, such as a common household current. A resilient outlet tube 36 having a select undeformed inner cross-sectional area extends from the collapsible bag 18 and a port 38 in the housing 14 and is in fluid communication with a patient administration set (not shown) to deliver therapeutic liquid from the collapsible bag 18 to a patient. As is well known in the art, liquid flows from the resilient outlet tube 36 by application of pressure from the inflatable bladder 20 upon the collapsible bag 18 within the chamber 16 of fixed volume.

The servo valve 12 consists of an anvil 40 and a blade 42 which receive a segment of the resilient outlet tube 36 therebetween. The anvil 40 consists of a portion of the wall of the housing 14 which defines the port 38 for the resilient outlet tube 36. The blade 42 is on the distal end 46 of an arm 48. The proximal end 50 of the arm 48 is pivotally attached to the housing 14. As illustrated in the preferred embodiment, arm 48 is rigid and the pivotal attachment is by a hinge 52. Alternatively, the housing and arm 14 could be integrally made of a suitable thermoplastic and the pivotal attachment could be a living hinge. A pressure pad 54 intermediate the proximal 50 and distal 46 ends of the arm 48 extends through an orifice 56 in the housing 14. The face of the pressure pad 54 has a defined surface area which is in contact with the collapsible bag 18. A spring 58 is located at the distal end of the arm 48 and biases the blade toward the anvil 40 so as to collapse and therefore to close the interior of the resilient outlet tube 36 by applying a select force. As an alternative to the spring 58, if the pump is maintained in the orientation illustrated in FIG. 1, the weight of the arm can apply the select force. A sensor 60 is operatively associated with the arm 48 to detect movement of the arm 48, and thus the blade 42. The sensor 60 is connected by connector 62 to the microprocessor 30.

In operation, the inflatable bladder 20 is inflated by air delivered from the volumetric air pump 26 through the conduit 22 to the bladder 20. As the bladder inflates, it applies pressure to the collapsible bag 18 which tends to cause therapeutic liquid to flow out the resilient tube 36. However, the valve 12 does not permit flow of liquid through the resilient tube 36 until the sufficient pressure builds up within the collapsible bag 18 to apply enough force to the pressure pad 54 to counter the bias of the spring 58 sufficiently to open the interior of the resilient outlet tube 36. Thus, a threshold pressure, preferably 9 psi, is necessary to counter the threshold force. The surface area of the pressure pad 54 is selected so that the select force is overcome when a desired threshold pressure is achieved in the collapsible bag 18. Once this threshold pressure is applied, gas is supplied to the inflatable bladder 20 at a substantially constant rate sufficient to provide a desired rate of flow to the patient through the resilient outlet tube. Assuming a 9 psi threshold pressure, the flow of air to the inflatable bladder 20 necessary to sustain a desired flow rate can be calculated as follows:

$$\frac{\text{Flow rate}}{\text{to bladder}} = \frac{\text{Desired Therapeutic Liquid Flow Rate} \times \left( \begin{array}{c} \text{Ambient Air Pressure} \\ + \\ \text{Bag Pressure} \end{array} \right)}{\text{Ambient Pressure}}$$

Thus, by way of example, assuming a 9 psi threshold pressure and a desired flow rate of therapeutic liquid of 25 ml/hour and an ambient air pressure of 14 psi, the calculation is as follows:

$$\frac{25 \times (14+9)}{14} = 38 \text{ ml/hour (approximately)}$$

Upon entry of the desired flow rate by a user, through the input station 30, the microprocessor calculates the required air flow in accordance with this equation. In application, depending on how smooth flow rate from the air pump is, the valve tends to "float" in a position which maintains an equilibrium.

At the start of an infusion, the volumetric air pump 26 is operated at a maximum rate to inflate the bladder until sufficient pressure develops within the collapsible bag 18 that the arm 48 and therefore the blade 42 are caused to lift relative to the anvil 40. The initial movement of the arm is detected by the sensor 60 which sends a signal to the microprocessor 28 which in turn sends a signal to the encoded electric motor drive 27 which slows the encoded electronic motor to slow the delivery of gas to the bladder to the necessary rate calculated to provide the desired flow rate entered in the input station 30 through the resilient outlet tube. Thereafter, the pump works similarly to a pressure regulator in which the valve 12 opens and closes to maintain a desired pressure at the outlet tube 36. If resistance to flow within the patient administration set increases, for example by the pump being lowered relative to a point of infusion to a patient which thereby increases the pressure in the outlet tube 36 and within the collapsible bag 18, the blade 42 will move further away from the anvil 40, thereby temporarily increasing the effective inner cross-sectional area of the resilient tube 36 to allow more flow until the system pressure returns to the desired pressure at the outlet tube and the flow rate returns to the desired flow rate. Thus, the pump is self regulated. If an obstruction occurs in the patient administration set or blood vessel of the patient such that pressure builds on the system above a select maximum the sensor 60 will detect corresponding movement of the arm 48 and send a signal to the microprocessor which in turn will stop the electric motor 27 and sound an alarm.

What is claimed is:

1. An infusion pump comprising:
    a reservoir containing a therapeutic liquid to be infused, the reservoir having an outlet for the liquid;
    a volumetric air pump operatively associated with the reservoir to pressurize the reservoir; and
    means for preventing liquid flow through the liquid outlet until a select pressure is obtained in the outlet and thereafter varying an opening in the outlet to maintain the pressure in the reservoir at substantially the select pressure, whereby the volumetric flow rate of liquid through the outlet is proportional to the volumetric flow rate of air from the volumetric air pump.

2. The infusion pump of claim 1 wherein the outlet comprises a flexible conduit and the valve varies the opening in the outlet by pinching a segment of the conduit to vary an inner cross-sectional area of the segment of the conduit.

3. The infusion pump of claim 1 wherein the reservoir comprises a collapsible wall and further comprising an inflatable bladder juxtaposed with the collapsible wall of the reservoir, the volumetric air pump being in fluid communication with the bladder.

4. The infusion pump of claim 3 wherein the volumetric air pump provides gas to the bladder at a first rate until the select pressure is applied to the reservoir and thereafter provides gas to the bladder at a second substantially uniform rate less than the first rate.

5. An infusion pump comprising:
    a reservoir containing a therapeutic liquid to be infused, the reservoir having an outlet for the liquid;
    a volumetric air pump operatively associated with the reservoir to pressurize the reservoir;
    a valve operatively associated with the liquid outlet; and
    a mechanical linkage between the reservoir and the valve causing the valve to prevent liquid flow through the liquid outlet until a select pressure is obtained in the reservoir and thereafter causing the valve to vary an opening in the outlet to maintain the pressure in the reservoir at substantially the select pressure.

6. The infusion pump of claim 5 wherein the valve comprises:
    a blade and an anvil receiving the liquid outlet therebetween.

7. The infusion pump of claim 6 wherein the mechanical linkage comprises:
    an arm having a distal end attached to the blade and a proximal end pivotally attached to a rigid housing, the arm including a pressure pad between the proximal and distal ends in contact with the reservoir.

8. The infusion pump of claim 7 further comprising a spring biasing means operatively associated with the arm.

9. The infusion pump of claim 6 wherein the volumetric air pump pressurizes the reservoir at a first rate until the select pressure sufficient to overcome a biasing force on the blade so as to initially move the blade away from the anvil is applied to the reservoir and thereafter the volumetric air pump pressurizes the reservoir at a second substantially uniform rate less than the first rate.

10. The infusion pump of claim 9 further comprising a detector operatively associated with the arm and the volumetric air pump, the detector detecting the initial movement of the arm and sending a first signal to the volumetric air pump.

11. The infusion pump of claim 10 wherein if the blade moves more than a select distance from the anvil a second signal is sent to the volumetric air pump.

12. The infusion pump of claim 7 wherein the mechanical linkage further comprises means for providing a force biasing the blade toward the anvil.

13. The infusion pump of claim 5 wherein the volumetric air pump pressurizes the reservoir at a first rate until the select pressure is obtained in the reservoir and thereafter the volumetric air pump pressurizes the reservoir at a second substantially uniform rate less than the first rate.

14. A method of infusing therapeutic liquid to a patient comprising:
    a) providing a reservoir containing a therapeutic liquid and having a liquid outlet;
    b) providing a volumetric air pump in operative association with the reservoir to pressurize the reservoir;
    c) maintaining a select pressure in the reservoir by varying an opening in the liquid outlet by means of a valve which is mechanically linked to the reservoir so that a flow of liquid through the liquid outlet is proportional to a volumetric flow rate of the volumetric air pump.

15. The method of claim 14 wherein in step a) the liquid outlet comprises a resilient tube and step c) further comprises applying a pinching force to a segment of the resilient tube and decreasing the pinching force as the pressure in the reservoir increases to increase an effective inner cross-sectional area of the segment of the resilient tube.

16. The method of claim 14 wherein in step a) the liquid outlet comprises a resilient tube and the reservoir is collapsible and step b) further comprises pressurizing the reservoir by providing a bladder juxtaposed with the reservoir in fluid communication with the volumetric air pump, the method further comprising:
    d) preventing flow of liquid through the liquid outlet if the pressure in the reservoir is less than the select pressure.

17. The method of claim 16 further comprising:
    e) inflating the bladder at a first rate until the select pressure is reached in the reservoir and thereafter inflating the bladder at a second substantially constant rate less than the first rate.

* * * * *